US 9,078,981 B2

(12) United States Patent
Subramaniam et al.

(10) Patent No.: US 9,078,981 B2
(45) Date of Patent: Jul. 14, 2015

(54) CATHETER SYSTEM INCLUDING AN EMBOLISM PROTECTION DEVICE

(71) Applicant: Boston Scientific Scimed Inc., Maple Grove, MN (US)

(72) Inventors: Raj Subramaniam, Fremont, CA (US); Kurt D. Sparks, San Carlos, CA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 15 days.

(21) Appl. No.: 14/031,164

(22) Filed: Sep. 19, 2013

(65) Prior Publication Data

US 2014/0088503 A1     Mar. 27, 2014

Related U.S. Application Data

(60) Provisional application No. 61/703,882, filed on Sep. 21, 2012.

(51) Int. Cl.
| | |
|---|---|
| *A61M 5/36* | (2006.01) |
| *A61M 25/06* | (2006.01) |
| *A61M 1/36* | (2006.01) |
| *A61M 39/28* | (2006.01) |

(52) U.S. Cl.
CPC .............. *A61M 5/36* (2013.01); *A61M 1/3627* (2013.01); *A61M 25/0662* (2013.01); *A61M 39/281* (2013.01)

(58) Field of Classification Search
CPC ..... A61M 5/36; A61M 5/365; A61M 5/3627; A61M 5/16831; A61M 2205/12; A61M 25/0662; A61M 1/3627; A61M 2039/205; A61M 2005/3123; A61M 39/281; A61M 2039/282

USPC ................................. 604/122; 96/6
See application file for complete search history.

(56) References Cited

U.S. PATENT DOCUMENTS

| | | | | |
|---|---|---|---|---|
| 2,937,643 | A | * | 5/1960 | Elliot ............................ 604/163 |
| 3,812,482 | A | | 5/1974 | Clark |
| 3,974,681 | A | | 8/1976 | Namery |
| 4,000,739 | A | * | 1/1977 | Stevens ......................... 604/537 |
| 4,137,940 | A | | 2/1979 | Faisandier |
| 4,280,495 | A | | 7/1981 | Lampert |
| 4,312,341 | A | | 1/1982 | Zissimopoulos et al. |
| 4,344,429 | A | | 8/1982 | Gupton et al. |
| 4,487,601 | A | | 12/1984 | Lindemann |

(Continued)

FOREIGN PATENT DOCUMENTS

| | | |
|---|---|---|
| WO | WO2007089309 A2 | 8/2007 |
| WO | WO2011142994 A2 | 11/2011 |

*Primary Examiner* — Manuel Mendez
(74) *Attorney, Agent, or Firm* — Faegre Baker Daniels LLP (57) ABSTRACT

The present invention relates to a device for the prevention of air embolisms during a catheterization procedure. The device includes a bulb element configured to secure to a sheath assembly. The bulb element includes a flexible wall, including a proximal section and a distal section, and an interior chamber in fluid communication with a pressurized fluid source. The proximal section of the bulb element includes a proximal hub, and the distal section of the bulb element includes a distal hub. The bulb element is collapsible, under the action of an external force, from a first, relaxed state in which the interior chamber has a first volume, to a second, collapsed state in which the interior chamber has a second volume less than the first volume, and wherein the bulb element is configured to assume its first, relaxed state in the absence of the external force.

18 Claims, 3 Drawing Sheets

(56) References Cited

U.S. PATENT DOCUMENTS

| | | | |
|---|---|---|---|
| 4,784,643 A | 11/1988 | Siretchi et al. | |
| 4,787,882 A * | 11/1988 | Claren | 604/6.16 |
| 4,895,346 A * | 1/1990 | Steigerwald | 251/149.1 |
| 4,898,586 A * | 2/1990 | McDonough | 604/171 |
| 5,152,277 A * | 10/1992 | Honda et al. | 600/116 |
| 5,376,077 A | 12/1994 | Gomringer | |
| 5,405,336 A * | 4/1995 | Austin et al. | 604/534 |
| 5,460,616 A * | 10/1995 | Weinstein et al. | 604/167.03 |
| 5,662,616 A * | 9/1997 | Bousquet | 604/175 |
| 5,695,474 A * | 12/1997 | Daugherty | 604/162 |
| 5,895,376 A | 4/1999 | Schwartz et al. | |
| 6,375,640 B1 * | 4/2002 | Teraoka | 604/263 |
| 6,569,158 B1 | 5/2003 | Abboud et al. | |
| 7,935,102 B2 | 5/2011 | Breznock et al. | |
| 8,025,640 B2 * | 9/2011 | Blier | 604/167.01 |
| 8,448,992 B2 * | 5/2013 | Min et al. | 285/3 |
| 8,882,745 B2 * | 11/2014 | Devellian et al. | 604/539 |
| 2005/0027253 A1 * | 2/2005 | Castellano et al. | 604/122 |
| 2010/0010442 A1 | 1/2010 | Shivkumar et al. | |

\* cited by examiner

CATHETER SYSTEM INCLUDING AN EMBOLISM PROTECTION DEVICE

CROSS-REFERENCE TO RELATED APPLICATION

This application claims the benefit of U.S. Provisional Application No. 61/703,882, filed Sep. 21, 2012, which is incorporated herein by reference in its entirety.

TECHNICAL FIELD

The present invention relates to medical devices, and more particularly, catheterization systems and methods for accessing an anatomical space within a body.

BACKGROUND

Various medical procedures require the use of introducers for introducing medical devices and instruments to targeted organs to be treated. Various techniques can be employed to minimize the likelihood of introducing air or other gases into the patient during such procedures. There is a continuing need for improved introducer systems and related instrumentation.

Owing to some interventional procedures that require vascular access, a patient can be catheterized through a vein or artery and a catheter can be routed to the heart or any other cardiovascular region. Many procedures, for example, aortic valve replacement, mitral valve repair, mitral appendage occlusion, etc., may require to be performed via catheters. The initial steps can involve placement of a hollow device within a blood vessel. The hollow device can be a sheath or a catheter. The hollow device is inserted into the body of a patient such that a proximal end of the device is outside the body and a distal of the device is inside the body. The proximal end of the hollow device can then be pushed so as to actuate the distal end of the hollow device farther into the blood vessel. A situation can be formed where a pressure difference can occur between the proximal end and the distal end of the device. If the pressure at the proximal end is greater than the pressure at the distal end, a negative pressure gradient can be formed or a pressure drop can occur. A low pressure can be created at the wake of the hollow device and this pressure difference can cause air to leak into the hollow device. Also, when the hollow device is pushed faster, a vacuum can be created inside the hollow device due to the pressure difference and this vacuum creation can cause air to leak into the hollow device. In such a case, air could escape into the blood stream of the patient in the form of air bubbles resulting in air embolism. An attempt to flush the hollow device, after the air bubbles have reached the distal end of the device, can push the air into the patient. Often, even an experienced operator may not be aware of the air introduction until it is already in a fluoroscopic area. As more complex and bulky devices are delivered, the risk of introduction of air into the patient can increase. Therefore, air needs to be trapped and removed before it reaches the distal end of the device.

Devices available for removing air can involve the use of stopcocks, adjustable valves, and various other devices. Owing to creation of high pressure or vacuum, these devices can be more prone to malfunction or failure as both vacuum and high pressure would increase stress on any of these devices. Malfunction or failure of these devices can lead to air embolism, thereby posing a serious threat to the patient. Hence, there is need for a device that can prevent air embolism with minimal and non-vital dependence on valves, stopcocks, screws, and other similar devices.

SUMMARY

In Example 1, the present invention is a device for use in combination with a sheath assembly for inhibiting air embolisms during a catheterization procedure, the sheath assembly including an interior lumen having a proximal opening. The device comprises a seal liquid source containing a seal liquid, and a bulb element. The bulb element is configured to be secured to the sheath assembly, and has a proximal section and a distal section and includes a flexible, resilient outer wall surrounding an interior chamber in fluid communication with the seal liquid source. The bulb element further includes a proximal hub on the proximal section of the bulb element, the proximal hub including a proximal hub opening, and a distal hub on the distal section of the bulb element opposite the proximal hub, the distal hub including a distal hub opening and being configured for coupling the device to the sheath assembly. The interior chamber is positioned between the proximal and distal hubs. The proximal and distal hub openings are positioned such that, when the device is coupled to the sheath assembly, the proximal and distal hub openings are generally axially aligned with the proximal opening of the interior lumen of the sheath assembly. Additionally, the bulb element is configured to allow introduction of the seal liquid into the interior chamber to substantially fill the interior chamber with the seal liquid thereby inhibiting the introduction of gas into the interior lumen of the sheath as an elongate medical device is inserted through the interior chamber and into the interior lumen of the sheath.

In Example 2, the device of Example 1, wherein the bulb element is collapsible, under the action of an external force, from a first, relaxed state in which the interior chamber has a first volume, to a second, collapsed state in which the interior chamber has a second volume less than the first volume, and wherein the bulb element is configured to assume its first, relaxed state in the absence of the external force.

In Example 3, the device of Examples 1 or 2, wherein the distal hub includes a means for releasably securing the bulb element to the sheath assembly.

In Example 4, the device of any of Examples 1-3, wherein the distal hub comprises at least one of a snap fit mechanism, a fixed coupler, or a rotating connector for securing the bulb element to the sheath assembly.

In Example 5, the device of any of Examples 1-4, wherein the bulb element includes an inlet port through the outer wall for fluidly coupling the interior chamber of the bulb element to the seal liquid source.

In Example 6, the device of any of Examples 1-5, wherein the seal liquid source includes a liquid reservoir or a saline drip line.

In Example 7, the device of any of Examples 1-6, wherein the proximal hub and distal hub each include a seal member configured to seal around an elongate medical instrument inserted through proximal and distal hub openings and the interior chamber of the bulb element.

In Example 8, the device of any of Examples 1-7, wherein the proximal hub and distal hub are aligned with each other along a longitudinal axis of the bulb element.

In Example 9, the device of any of Examples 1-8, wherein the proximal hub is aligned with and positioned adjacent to the distal hub in the first, collapsed state.

In Example 10, the device of any of Examples 1-9, wherein the outer wall of the bulb element comprises a transparent or translucent material.

In Example 11, the device of any of Examples 1-10, further comprising an outer shell having a relatively rigid outer wall disposed about and surrounding the bulb element.

In Example 12, the device of Example 11, wherein the outer shell includes first and second sections telescopically connected to one another to accommodate changes in volume of the bulb element.

In Example 13, a catheter system configured to inhibit the formation of air embolisms during a catheterization procedure. The catheter system comprises an introducer sheath assembly, a hemostasis mechanism, and an embolism protection device. The introducer sheath assembly includes an elongate tubular shaft having a proximal section and an opposite distal section, and an interior lumen extending longitudinally through the proximal and distal sections of the shaft. The hemostasis mechanism is coupled to the proximal section of the shaft and includes an access opening and a seal member configured to slidably receive and seal around an elongate device extendable therethrough, the access opening generally axially aligned with the interior lumen of the shaft. The embolism protection device includes a seal liquid source containing a seal liquid, and a bulb element. The bulb element is secured to the sheath assembly, and has a proximal section and a distal section and includes a flexible, resilient outer wall surrounding an interior chamber in fluid communication with the seal liquid source. The bulb element further includes a proximal hub on the proximal section of the bulb element, the proximal hub including a proximal hub opening. The bulb element also includes a distal hub on the distal section of the bulb element opposite the proximal hub, the distal hub including a distal hub opening and being configured for coupling the device to the sheath assembly, the interior chamber being positioned between the proximal and distal hubs. The proximal and distal hub openings are positioned such that, when the device is coupled to the sheath assembly, the proximal and distal hub openings are generally axially aligned with the proximal opening of the interior lumen of the sheath assembly. In addition, the bulb element is configured to allow introduction of the seal liquid into the interior chamber to substantially fill the interior chamber with the seal liquid thereby inhibiting the introduction of gas into the interior lumen of the sheath as an elongate medical device is inserted through the interior chamber and into the interior lumen of the sheath.

In Example 14, the catheter system of Example 13, wherein the bulb element is collapsible, under the action of an external force, from a first, relaxed state in which the interior chamber has a first volume, to a second, collapsed state in which the interior chamber has a second volume less than the first volume, and wherein the bulb element is configured to assume its first, relaxed state in the absence of the external force.

In Example 15, a catheterization method comprising first positioning a sheath assembly coupled to an embolism protection device at a selected location within a patient's anatomy, the sheath assembly including an inner lumen and the embolism protection device including a bulb element coupled to the sheath assembly, the bulb element having a proximal section and a distal section and including a flexible, resilient outer wall surrounding an interior chamber in fluid communication with a seal liquid source, wherein the bulb element is in a relaxed state in which the interior chamber has a first volume. Next, the method comprises causing or allowing seal liquid from the seal liquid source to substantially fill the interior chamber of the bulb element. The method then comprises compressing the bulb element to a first, collapsed state to compress a proximal section of the bulb element against a distal section of the bulb element and reduce the volume within the interior chamber to a second volume less than the first volume, wherein in the collapsed state proximal and distal openings of the bulb element are positioned adjacent to and axially aligned with one another and the inner lumen of the sheath assembly. Next, a medical device is inserted through the interior chamber and into the inner lumen of the sheath assembly. The method further comprises then allowing the bulb element to resume its relaxed state in which the interior chamber substantially returns to its first volume, wherein the interior chamber remains substantially filled with the seal liquid. In the method of Example 15, the presence of the seal liquid within the interior chamber inhibits the introduction of air into the interior lumen of the sheath assembly about the medical device.

In Example 16, the method of Example 15, wherein actuating the bulb element includes squeezing the proximal section of the bulb element against the distal section of the bulb element.

In Example 17, the method of Examples 15 or 16, further comprising flushing the bulb element with the seal liquid to purge an air bolus from the interior chamber.

In Example 18, the method of any of Examples 15-17, wherein the bulb element is releasably coupled to the sheath assembly.

In Example 19, the method of any of Examples 15-18, wherein the proximal section of the bulb element includes a proximal hub and the distal section of the bulb element includes a distal hub, and wherein the proximal and distal hubs each include at least one of a snap fit mechanism, a fixed coupler, or a rotating connector, and wherein coupling the bulb element to the sheath assembly comprises releasably securing the bulb element to the sheath assembly.

In Example 20, the method of any of Examples 15-19, wherein the sheath assembly includes at least one hemostasis valve, and wherein the bulb element is releasably secured to the hemostasis valve.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
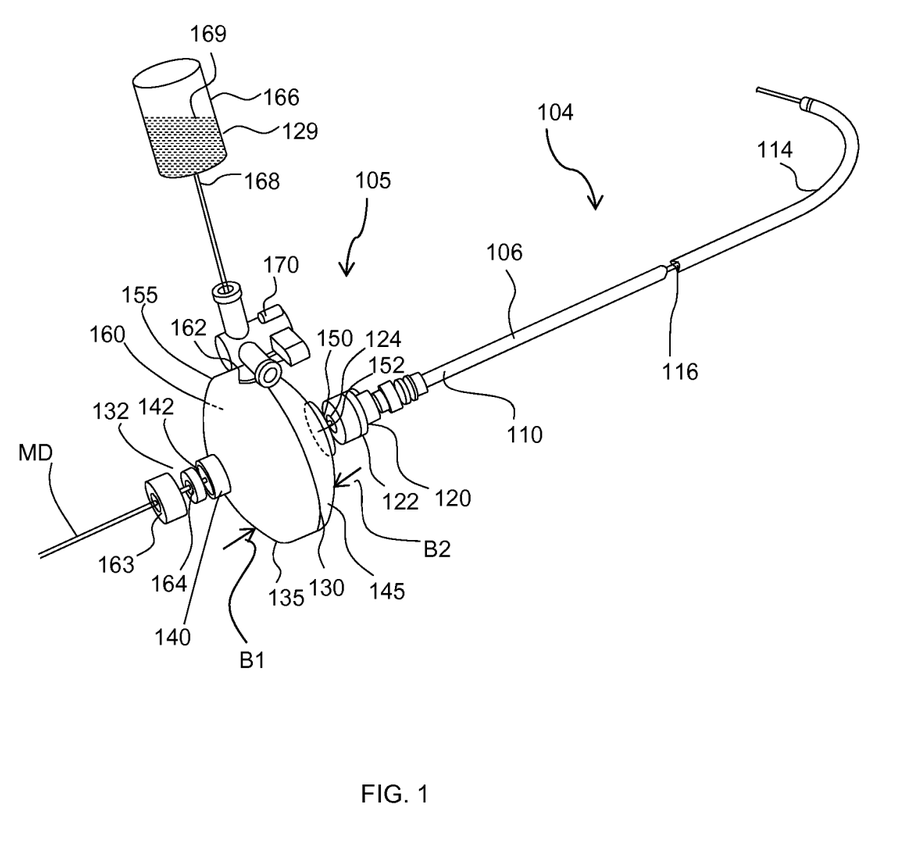
FIG. 1 is a schematic illustration an exemplary catheter device that can be used in relation to embodiments of the present invention.

FIG. 1 is a schematic illustration of an exemplary catheter system 100 that can be used in relation to embodiments of the present invention. As shown in FIG. 1, the catheter system 100 includes a sheath assembly 104 and an embolism protection device 105 coupled to the sheath assembly 104. In the illustrated embodiment, for illustration purposes, certain components of the sheath assembly 104 and the embolism protection device 105 are shown in an exploded, unassembled view. In various embodiments, the catheter system 100 can be utilized for introducing various medical devices and instruments into the patient anatomy for a variety of interventional and therapeutic procedures including, without limitation, electrophysiology procedures, inverventional cardiology procedures, and the like. For illustration purposes, an exemplary medical device MD (e.g., a guide wire, stylet, catheter, electrode lead, and the like) is shown inserted into the catheter system 100. In various embodiments, depending on the particular procedure being performed, the distal portion of the sheath assembly 104 can be advanced to the particular organ or area of interest within the patient's body, and thereafter operates as a conduit for subsequent introduction of the MD to the target organ as may be required for the particular procedure being performed. As will be explained in greater detail below, the embolism protection device 105 operates to substantially inhibit the formation and subsequent transmission of air or other gas emboli through the sheath assembly 104 and into the patient as the MD is advanced through and withdrawn from the sheath assembly 104.

In various embodiments, the sheath assembly 104 includes an elongate tubular shaft 106 having a proximal section 110, a distal section 114, and an inner lumen 116 extending therethrough. As further shown, a hemostasis mechanism 120 is coupled to the proximal section 114 of the shaft 106, and includes a housing 122, an access opening 124 and a seal member (not shown in FIG. 1) contained within the housing 122. The hemostasis mechanism 120 is, in various embodiments, configured to slidably receive and seal around an elongate device, e.g., the device MD, that is extended therethrough. In the various embodiments, the access opening 124 is generally axially aligned with the interior lumen 116 of the shaft 106. In the illustrated embodiment, the hemostasis mechanism 120 is separately coupled to the proximal section 110 of the shaft 106, and may be removable therefrom. In various other embodiments, however, the hemostasis mechanism 120 can be integrally formed with the shaft 106 and/or can be permanently attached thereto. In short, any hemostasis mechanism configuration for use with an introducer sheath, whether now known or later developed, can be utilized with the catheter device 100 of the various embodiments.

As further shown in FIG. 1, the embolism protection device 105 includes a seal liquid source 129, a bulb element 130, and a proximal hemostasis valve 132. In addition, the bulb element 130 includes a proximal section 135 having a proximal hub 140 with a proximal opening 142, a distal section 145 having a distal hub 150 with a distal hub opening 152, an outer wall 155 surrounding and defining an interior chamber 160, and an inlet port 162. In the illustrated embodiment, the proximal and distal hubs 140, 150 are positioned opposite one another with the interior chamber 160 therebetween. In addition, the proximal and distal hubs 140, 150 are generally axially aligned with one another and with the interior lumen 116 of the shaft 106. The proximal and distal hub openings 142, 152 are thus also generally axially aligned with the lumen 116, thus providing a relatively straight pathway for insertion of the MD into the lumen 116.

In the illustrated embodiment, the proximal hemostasis valve 132 includes an end cap 163 and a proximal seal member 164. As can be seen in FIG. 1, when the proximal hemostasis valve 132 is assembled, the end cap 163 secures the proximal hemostasis valve 132 to the proximal hub 140 of the bulb element 130. When present, the proximal hemostasis valve 132 operates to seal around the MD when it is advanced through the embolism protection device 105, and also inhibits unintended loss of fluid from and/or fluid ingress into the lumen 116 of the sheath assembly 104.

In the illustrated embodiment, the distal hub 150 can be configured to couple the bulb element 130 to the hemostasis mechanism 120. In various other embodiments, a distal hemostasis valve (not shown) can be coupled to the distal hub 150 in addition to or in lieu of the hemostasis mechanism 120. In embodiments configured to connect to the hemostasis mechanism 120 on the sheath assembly 104, the distal hub 150 can include coupling features designed to releasably engage the housing 122 of the hemostasis mechanism 120. For example, the distal hub 150 can include a snap fit mechanism, a fixed coupler, a rotating connector, or any other similar mechanism or fastener for securing the distal hub 150 to the hemostasis mechanism 120 and/or to the sheath assembly 104.

The inlet port 162 is configured to fluidly couple the interior chamber 160 of the bulb element 130 to the seal liquid source 129. In various embodiments, the inlet port 162 includes an opening through the outer wall 155 of the bulb element.

In various embodiments, as illustrated in FIG. 1, the seal liquid source 129 includes a liquid reservoir 166, a supply tube 168, and a control valve 170, e.g., a stopcock coupled to the inlet port 162 of the bulb element. The liquid reservoir 166, supply tube 168 and the inlet port 162 of the bulb element 130 are all in fluid communication with one another to supply a seal liquid 169 (e.g., saline) to the interior chamber 160 of the bulb element. In various embodiments, the liquid reservoir 166 and the supply tube 168 can be in the form of a saline IV bag and a saline drip line, respectively. The control valve 170 can operate to control the flow of the seal liquid 169 to the interior chamber 160.

In an various embodiments, the bulb element 130 is configured to allow introduction of the seal liquid into the interior chamber 160 to substantially fill the interior chamber with the seal liquid 169 thereby inhibiting the introduction of gas into the interior lumen 116 of the sheath assembly 104, which could otherwise form an embolism in the patient, as an elongate medical device MD is inserted through the interior chamber 160 and into the interior lumen 116 of the sheath assembly 104. That is, in various embodiments, the presence of the seal liquid 169 operates as a liquid seal around the outer surface of the MD as it is advanced into and withdrawn from the lumen 116. Thus, even if a vacuum is formed within the interior chamber 160 (e.g., by the action of withdrawing the MD from the lumen 116), the interior chamber 160 will be filled with the seal liquid 169 rather than ambient air or other gas. In various embodiments, the entire catheter system 100 can be purged with saline or other liquid to remove any bolus of air or other gas that may be present within the interior chamber 160 prior to use.

In various embodiments, the outer wall 155 of the bulb element 130 can be made from a flexible, resilient elastomeric material. In an embodiment, the elastomeric material forming the outer wall 155 can be a translucent or transparent material. The transparent or translucent material can be used to detect any presence of air emboli during the catheterization process such as to enable appropriate action for removing the air emboli from the catheter system 100.

In various embodiments, the bulb element 130 is collapsible, under the action of an external force, from a first, relaxed state in which the interior chamber 160 has a first volume, to a second, collapsed state in which the interior chamber 160 has a second volume less than the first volume. In various embodiments, the outer wall 155 is both flexible and resilient such that the bulb element 130 is configured to return to its first, relaxed state in the absence of the external force. Thus, in use, the clinician can apply a force (as indicated by the arrows B1 and B2 in FIG. 1) to squeeze the proximal and distal sections 135, 145 toward one another, thus collapsing the bulb element 130 and reducing the interior volume of the interior chamber 160. In various embodiments, this collapsing action is generally in the axial direction, such that the proximal and distal hubs 140, 150, and consequently, the proximal and distal hub openings 142, 152, will be urged to positions proximate and generally axially aligned with one another, thus facilitating ease of insertion of the MD into the embolism protection device 105 and the sheath lumen 116.

In addition, act of collapsing the bulb element 130 will operate to substantially purge the interior chamber 160 of seal liquid 169 and any air or other gas contained therein, which will be vented from the interior chamber 160 into the liquid reservoir 166. When the collapsing force is released, i.e., after the medical device MD has been advanced into the sheath lumen 116, the resiliency of the outer wall 155 will cause the bulb element 130 to return to its relaxed state and initial volume. Due to the fluid coupling of the interior chamber 160 and the seal liquid source 129, however, the interior chamber 160 will be substantially filled with the seal liquid 169 as it returns to its relaxed state. The seal liquid 169 thus maintains a liquid seal around the MD as it is further advanced into and/or withdrawn from the lumen 116.

Figure 2:
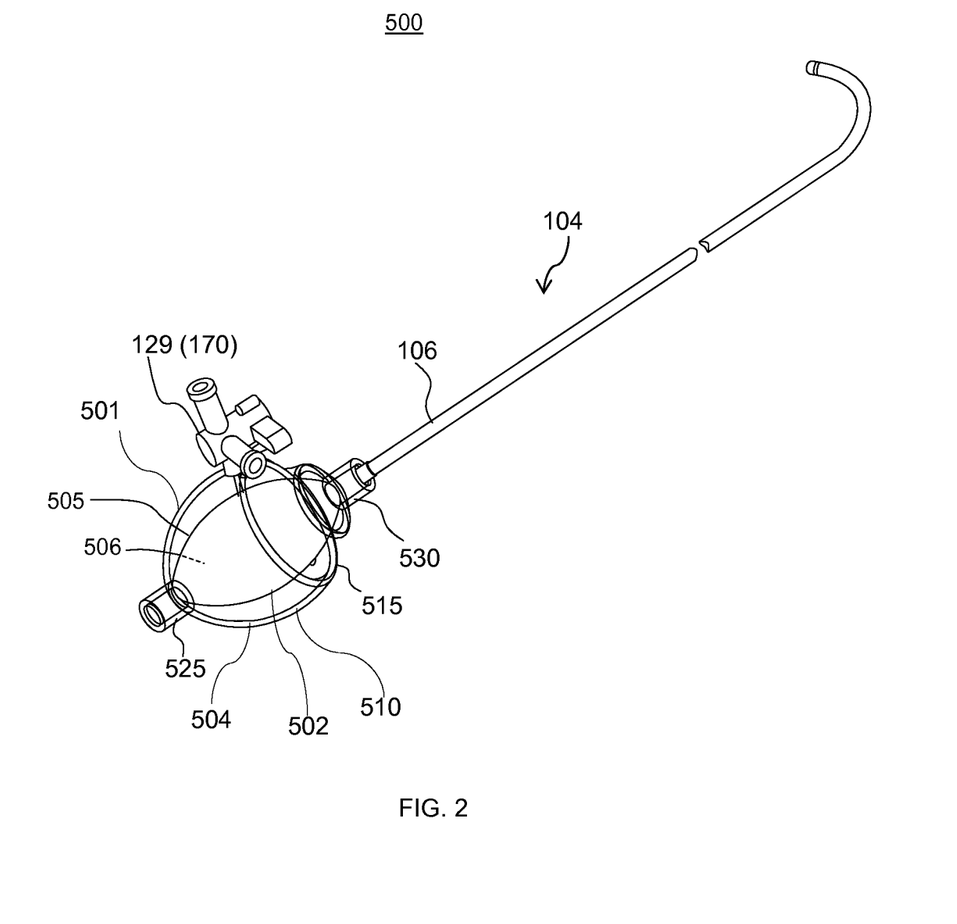
FIG. 2 is a schematic illustration of an exemplary alternative catheter device according to another embodiment of the present invention.

FIG. 2 illustrates an exemplary alternative catheter system 500 according to another embodiment of the present invention configured to inhibit the formation of air embolisms during a catheterization procedure. As shown in FIG. 2, the catheter system 500 can include the sheath assembly 104 and an alternative embolism protection device 501. Like the catheter system 100, the catheter system 500 is configured to facilitate the introduction of other elongate medical devices (e.g., guide wires, stylets, catheters, and the like) to a target organ in a patient, while substantially inhibiting or preventing the introduction of air or other gas embolisms to the patient.

In the illustrated embodiment, the embolism protection device 501 includes a bulb element 502, an outer shell 504 and the seal liquid source 129 (for illustration purposes, only the control valve 170 is shown in FIG. 2). In an embodiment, the bulb element 502 includes a flexible outer wall 505 defining and surrounding an interior chamber 506, and is configured to operate in substantially the same or an identical manner as the bulb element 130 of the embolism protection device 105 discussed above. That is, the interior chamber 506 is in fluid communication with the seal liquid 169 of the seal liquid source 129 (see FIG. 1), which operates to provide a liquid seal around a medical device when inserted into or withdrawn from the lumen of the introducer sheath assembly 104. Additionally, like the bulb element 130, the outer wall 505 is flexible and resilient such that the bulb element 502 is collapsible from a relaxed state in which the interior chamber 506 has a first volume, to a collapsed state in which the interior chamber 506 has a second volume less than the first volume, with the resiliency of the outer wall 505 causing the bulb element 502 to be biased toward its relaxed state.

In the illustrated embodiment, the outer shell 504 is radially disposed around the bulb element 502. In various embodiments, the outer shell 504 can include separate proximal and distal portions 510, 515 that are slidably coupled to one another such that they can telescope relative to one another to accommodate compression and subsequent re-expansion of the bulb element 502. The outer shell 504 can be configured to provide a protective covering to the bulb element 502. In various embodiments, one or both of the outer wall 505 of the bulb element 502 and the outer shell 504 can be made of a substantially transparent or translucent material to facilitate visualization of any air or gas bubbles that may form in the interior chamber 506.

In various embodiments, embolism protection device 501 includes a proximal hub 525 on the proximal portion 510 of the outer shell 504, and a distal hub 530 on the distal portion 515 of the outer shell 504. In various embodiments, the proximal hub 525 and/or the distal hub 530 can each include a hemostasis seal similar to those described above in connection with the embolism protection device 105. In various embodiments, the distal hub 530 can be configured to and include means to releasably couple the embolism protection device 501 to the sheath assembly 104. In various embodiments, the embolism protection device 501 can be fixedly and permanently attached to the sheath assembly 104, or to a hemostasis mechanism (such as the hemostasis mechanism 120) on the sheath assembly 104. In the various embodiments, the proximal and distal hubs 525, 530 are generally axially aligned with the inner lumen of the sheath assembly 104. Additionally, the telescoping configuration of the outer shell 504, and the compressibility of the bulb element 502, allows the proximal and distal hubs 525, 530 to be urged so as to be adjacent to and axially aligned with one another and the inner lumen to facilitate ease of insertion and/or withdrawal of an elongate medical device into/from the lumen of the sheath assembly 104.

Figure 3:
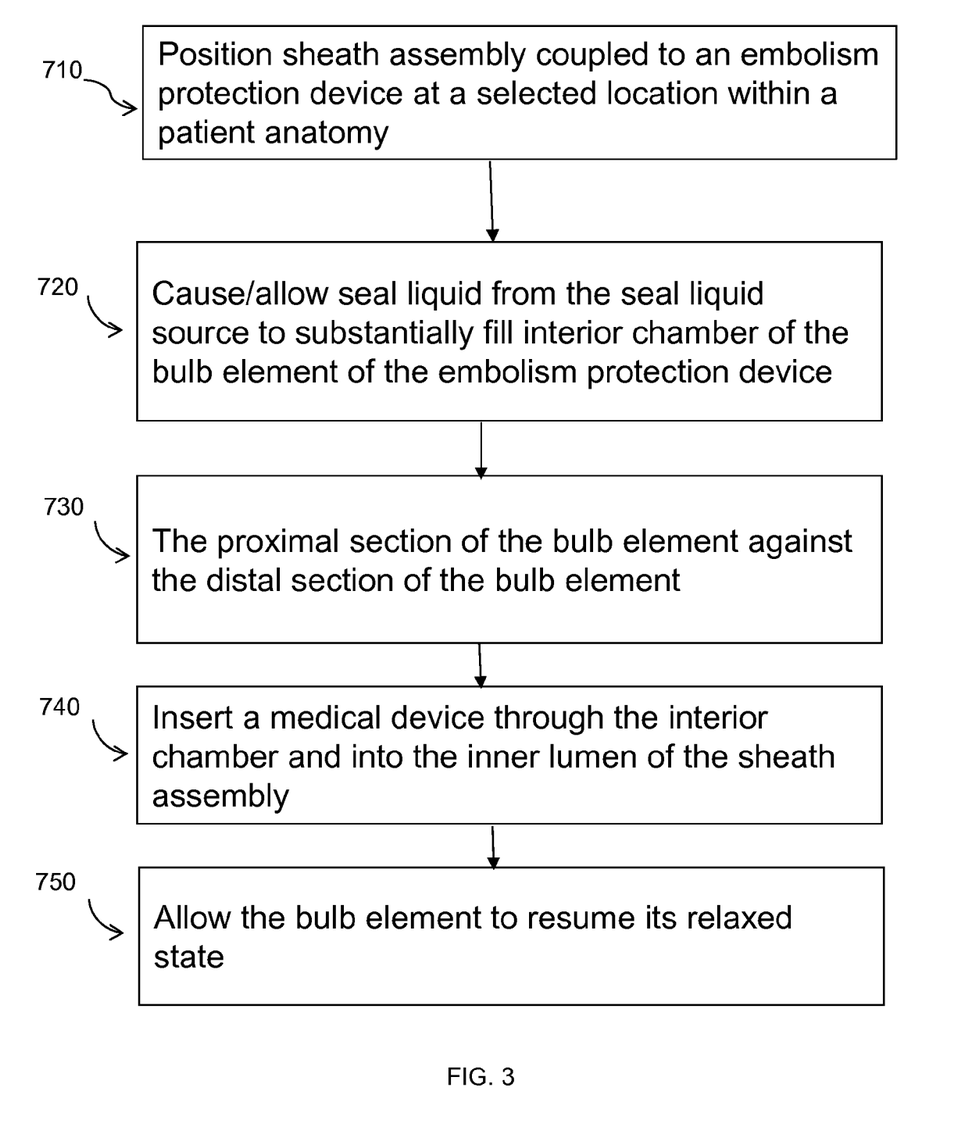
FIG. 3 is a flowchart illustrating a method of preventing air embolisms during a catheterization procedure according to an embodiment of the present invention.

FIG. 3 is a flow diagram showing an illustrative method 700 of preventing the introduction of air into a body of a patient during a catheterization procedure using, for example, the catheter devices 100 or 500 according to one embodiment. As shown in FIG. 3, the method 700 can include, at step 710 positioning a sheath assembly coupled to an embolism protection device 105, 501 at a selected location within a patient anatomy. Next, at step 720, the clinician can cause or allow seal liquid 169 from the seal liquid source to substantially fill the interior chamber 160, 506 of the bulb element 130, 502 of the embolism protection device 105, 501.

At step 730, the bulb element 130, 502 can be compressed to a first, collapsed state to compress the proximal section of the bulb element against the distal section of the bulb element and reduce the volume within the interior chamber, such that the proximal and distal openings of the bulb element are positioned adjacent to and axially aligned with one another and the inner lumen of the sheath assembly. In an embodiment, this step can be accomplished by squeezing the proximal section of the bulb element 130 or 502 against the corresponding distal section, as explained in detail with reference to FIG. 1 and FIG. 2, respectively. Next, at step 740, an elongate medical device can be into inserted the interior chamber and into the inner lumen of the sheath assembly.

As further shown in FIG. 3, the method 700 next includes, at step 750, allowing the bulb element 130, 502 to resume its relaxed state in which its interior chamber substantially returns to its relaxed state volume while remaining substantially filled with the seal liquid due to the fluid connection of the interior chamber and the seal liquid source.

In various embodiments, the method 700 can further include flushing the bulb element 130, 502 with the seal liquid 169 to vent any air bolus that may exist within the respective interior chamber.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A device for use in combination with a sheath assembly for inhibiting air embolisms during a catheterization procedure, the sheath assembly including an interior lumen having a proximal opening, the device comprising:
 a seal liquid source containing a seal liquid;
 a bulb element configured to be secured to the sheath assembly, the bulb element including:
  a proximal section and a distal section and including a flexible, resilient outer wall surrounding an interior chamber in fluid communication with the seal liquid source;
  a proximal hub on the proximal section of the bulb element, the proximal hub including a proximal hub opening;
  a distal hub on the distal section of the bulb element opposite the proximal hub, the distal hub including a distal hub opening and being configured for coupling the device to the sheath assembly, the interior chamber being positioned between the proximal and distal hubs;
 wherein the proximal and distal hub openings are positioned such that, when the device is coupled to the sheath assembly, the proximal and distal hub openings are generally axially aligned with the proximal opening of the interior lumen of the sheath assembly;
 wherein the bulb element is configured to allow introduction of the seal liquid into the interior chamber to substantially fill the interior chamber with the seal liquid thereby inhibiting the introduction of gas into the interior lumen of the sheath as an elongate medical device is inserted through the interior chamber and into the interior lumen of the sheath; and
 wherein the bulb element is collapsible, under the action of an external force, from a first, relaxed state in which the interior chamber has a first volume, to a second, collapsed state in which the interior chamber has a second volume that is less than the first volume and the seal liquid and gas in the interior chamber are purged from the interior chamber to the seal liquid source, wherein the bulb element is configured to assume its first, relaxed state in the absence of the external force to at least partially fill the interior chamber from the seal liquid source.

2. The device of claim 1, wherein the distal hub includes a means for releasably securing the bulb element to the sheath assembly.

3. The device of claim 1, wherein the distal hub comprises at least one of a snap fit mechanism, a fixed coupler, or a rotating connector for securing the bulb element to the sheath assembly.

4. The device of claim 1, wherein the bulb element includes an inlet port through the outer wall for fluidly coupling the interior chamber of the bulb element to the seal liquid source.

5. The device of claim 4, wherein the seal liquid source includes a liquid reservoir or a saline drip line.

6. The device of claim 1, wherein the proximal hub and distal hub each include a seal member configured to seal around an elongate medical device inserted through the proximal and distal hub openings and the interior chamber of the bulb element.

7. The device of claim 1, wherein the proximal hub and distal hub are aligned with each other along a longitudinal axis of the bulb element.

8. The device of claim 7, wherein the proximal hub is aligned with and positioned adjacent to the distal hub in the first, collapsed state.

9. The device of claim 1, wherein the outer wall of the bulb element comprises a transparent or translucent material.

10. The device of claim 1, further comprising an outer shell having a relatively rigid outer wall disposed about and surrounding the bulb element.

11. The device of claim 10, wherein the outer shell includes first and second sections telescopically connected to one another to accommodate changes in volume of the bulb element.

12. A catheter system configured to inhibit the formation of air embolisms during a catheterization procedure, the catheter system comprising:
 an introducer sheath assembly including:
  an elongate tubular shaft having a proximal section and an opposite distal section, and an interior lumen extending longitudinally through the proximal and distal sections of the shaft; and
  a hemostasis mechanism coupled to the proximal section of the shaft including an access opening and a seal member configured to slidably receive and seal around an elongate medical device extendable therethrough, the access opening generally axially aligned with the interior lumen of the shaft;
 an embolism protection device including:
  a seal liquid source containing a seal liquid;
  a bulb element secured to the sheath assembly, the bulb element having a proximal section and a distal section and including a flexible, resilient outer wall surrounding an interior chamber in fluid communication with the seal liquid source;
  a proximal hub on the proximal section of the bulb element, the proximal hub including a proximal hub opening; and
  a distal hub on the distal section of the bulb element opposite the proximal hub, the distal hub including a distal hub opening and being configured for coupling the device to the sheath assembly, the interior chamber being positioned between the proximal and distal hubs;
 wherein the proximal and distal hub openings are positioned such that, when the device is coupled to the sheath assembly, the proximal and distal hub openings are generally axially aligned with the proximal opening of the interior lumen of the sheath assembly;
 wherein the bulb element is configured to allow introduction of the seal liquid into the interior chamber to substantially fill the interior chamber with the seal liquid thereby inhibiting the introduction of gas into the interior lumen of the sheath as an elongate medical device is inserted through the interior chamber and into the interior lumen of the sheath; and
 wherein the bulb element is collapsible, under the action of an external force, from a first, relaxed state in which the interior chamber has a first volume, to a second, collapsed state in which the interior chamber has a second volume that is less than the first volume and the seal liquid and gas in the interior chamber are purged from the interior chamber to the seal liquid source, wherein the bulb element is configured to assume its first, relaxed state in the absence of the external force to at least partially fill the interior chamber from the seal liquid source.

13. A catheterization method comprising:

positioning a sheath assembly coupled to an embolism protection device at a selected location within a patient anatomy, the sheath assembly including an inner lumen and the embolism protection device including a bulb element coupled to the sheath assembly, the bulb element having a proximal section and a distal section and including a flexible, resilient outer wall surrounding an interior chamber in fluid communication with a seal liquid source, wherein the bulb element is collapsible, under the action of an external force, from a first, relaxed state in which the interior chamber has a first volume, to a second, collapsed state in which the interior chamber has a second volume that is less than the first volume;

causing or allowing seal liquid from the seal liquid source to substantially fill the interior chamber of the bulb element;

compressing the bulb element to the second, collapsed state to reduce the volume within the interior chamber to the second volume that is less than the first volume, wherein the seal liquid and gas in the interior chamber are purged from the interior chamber to the seal liquid source and proximal and distal openings of the bulb element are positioned adjacent to and axially aligned with one another and the inner lumen of the sheath assembly;

inserting a medical device through the interior chamber and into the inner lumen of the sheath assembly;

allowing the bulb element to resume its first, relaxed state in which the interior chamber substantially returns to the first volume to at least partially fill the interior chamber with the seal liquid from the seal liquid source; and wherein the presence of the seal liquid within the interior chamber inhibits the introduction of air into the interior lumen of the sheath assembly about the medical device.

14. The method of claim 13, wherein actuating the bulb element includes squeezing the proximal section of the bulb element against the distal section of the bulb element.

15. The method of claim 13, further comprising flushing the bulb element with the seal liquid to purge an air bolus from the interior chamber.

16. The method of claim 13, wherein the bulb element is releasably coupled to the sheath assembly.

17. The method of claim 13, wherein the proximal section of the bulb element includes a proximal hub and the distal section of the bulb element includes a distal hub, and wherein the proximal and distal hubs each include at least one of a snap fit mechanism, a fixed coupler, or a rotating connector, and wherein coupling the bulb element to the sheath assembly comprises releasably securing the bulb element to the sheath assembly.

18. The method of claim 17, wherein the sheath assembly includes at least one hemostasis valve, and wherein the bulb element is releasably secured to the hemostasis valve.

* * * * *